US008328744B2

(12) United States Patent  (10) Patent No.: US 8,328,744 B2
Farrell et al.  (45) Date of Patent: *Dec. 11, 2012

(54) DYNAMIC HAND SPLINTS

(75) Inventors: John Fletcher Farrell, Charlotte, NC (US); Henry B. Hoffman, Charlotte, NC (US)

(73) Assignee: Saebo, Inc., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/031,540

(22) Filed: Feb. 21, 2011

(65) Prior Publication Data

US 2011/0144552 A1  Jun. 16, 2011

Related U.S. Application Data

(63) Continuation of application No. 11/164,954, filed on Dec. 12, 2005, now Pat. No. 7,892,194.

(60) Provisional application No. 60/635,332, filed on Dec. 10, 2004.

(51) Int. Cl.
*A61F 5/00* (2006.01)

(52) U.S. Cl. ................. 602/21; 602/20; 601/40; 482/27

(58) Field of Classification Search .............. 602/20–22; 128/878–880; 482/27; 601/40

See application file for complete search history.

(56) References Cited

U.S. PATENT DOCUMENTS

| 867,981 A | 10/1907 | Krizek |
| 2,863,449 A | 12/1958 | Spencer |
| 3,631,542 A | 1/1972 | Potter |
| 3,769,970 A | 11/1973 | Swanson |
| 3,957,266 A | 5/1976 | Rice |
| 4,173,021 A | 10/1979 | Ziichner et al. |
| 4,602,620 A | 7/1986 | Marx |
| 4,765,320 A | 8/1988 | Lindemann et al. |
| 4,772,012 A | 9/1988 | Chesher |
| 4,781,178 A | 11/1988 | Gordon |

(Continued)

FOREIGN PATENT DOCUMENTS

DE  8804564.1 U1  9/1988

(Continued)

OTHER PUBLICATIONS

Office Action for EP Application No. 05853749.9, dated Mar. 28, 2011.

(Continued)

*Primary Examiner* — Loan Thanh
*Assistant Examiner* — Camtu Nguyen
(74) *Attorney, Agent, or Firm* — Nelson Mullins Riley & Scarborough, LLP

(57) ABSTRACT

A dynamic hand splint includes as elements thereof: a forearm support section and a hand support section that are configured to be releasably attached to a forearm; and one or more finger tensioners that are releasably attached to the hand support section and that are configured to be releasably attached to a respective finger such that, when the finger is flexed from an extended position toward a flexed position, the finger is urged by the finger tensioner toward an extended position. A method includes: attaching a forearm support section and a hand support section to a forearm; attaching finger tensioners to the hand support section; and attaching each of the finger tensioners to a respective finger such that, when the finger is flexed from an extended position toward a flexed position, the finger is urged by the finger tensioner toward an extended position.

19 Claims, 7 Drawing Sheets

U.S. PATENT DOCUMENTS

| | | | |
|---|---|---|---|
| 4,790,301 | A | 12/1988 | Silfverskiold |
| 4,858,903 | A | 8/1989 | Tari et al. |
| 4,865,285 | A | 9/1989 | Gaggianese |
| 4,875,469 | A | 10/1989 | Brook et al. |
| 4,881,275 | A | 11/1989 | Cazares et al. |
| 4,945,902 | A | 8/1990 | Dorer et al. |
| 4,949,711 | A | 8/1990 | Gyovai et al. |
| 4,960,114 | A | 10/1990 | Dale |
| 4,977,890 | A | 12/1990 | Mann |
| 5,056,504 | A | 10/1991 | Mann |
| 5,156,168 | A | 10/1992 | Canterna |
| 5,162,030 | A | 11/1992 | Tanski |
| 5,205,812 | A | 4/1993 | Wasserman |
| 5,263,593 | A | 11/1993 | Aida |
| 5,295,948 | A | 3/1994 | Gray |
| 5,413,554 | A | 5/1995 | Trueman |
| 5,415,623 | A | 5/1995 | Cherubini |
| 5,415,624 | A | 5/1995 | Williams |
| 5,447,490 | A | 9/1995 | Fula et al. |
| 5,453,064 | A | 9/1995 | Williams, Jr. |
| 5,456,650 | A | 10/1995 | Williams, Jr. et al. |
| 5,505,553 | A | 4/1996 | Saviano et al. |
| 5,514,052 | A | 5/1996 | Charles et al. |
| 5,538,488 | A | 7/1996 | Villepigue |
| 5,542,667 | A | 8/1996 | Lezdey et al. |
| 5,560,375 | A | 10/1996 | Kabanek |
| 5,584,799 | A | 12/1996 | Gray |
| 5,599,123 | A | 2/1997 | Still |
| 5,637,078 | A | 6/1997 | Varn |
| 5,697,103 | A | 12/1997 | Wiggins |
| 5,807,293 | A | 9/1998 | Wedge, Jr. |
| 5,820,577 | A | 10/1998 | Taylor |
| 5,836,902 | A | 11/1998 | Gray |
| 5,876,363 | A | 3/1999 | Marx |
| 5,921,945 | A | 7/1999 | Gray |
| 6,033,139 | A | 3/2000 | Dutcher |
| 6,561,995 | B1 | 5/2003 | Thibodo, Jr. |
| 6,702,725 | B2 | 3/2004 | Hoffman et al. |
| 6,854,913 | B2 | 2/2005 | Farrell et al. |
| 7,001,352 | B2 | 2/2006 | Farrell et al. |
| 7,892,194 | B2 * | 2/2011 | Farrell et al. .................... 602/21 |
| 2002/0077578 | A1 | 6/2002 | Bonutti |
| 2002/0198089 | A1 | 12/2002 | Hoffman et al. |
| 2003/0162634 | A1 | 8/2003 | Farrell et al. |
| 2003/0195093 | A1 | 10/2003 | White |
| 2003/0228185 | A1 | 12/2003 | Farrell et al. |

FOREIGN PATENT DOCUMENTS

| | | |
|---|---|---|
| DE | 9204652.5 U1 | 7/1992 |
| WO | 9403238 A | 2/1994 |

OTHER PUBLICATIONS

Search Report from corresponding European Application No. 05853749.9, dated Nov. 25, 2009.

* cited by examiner

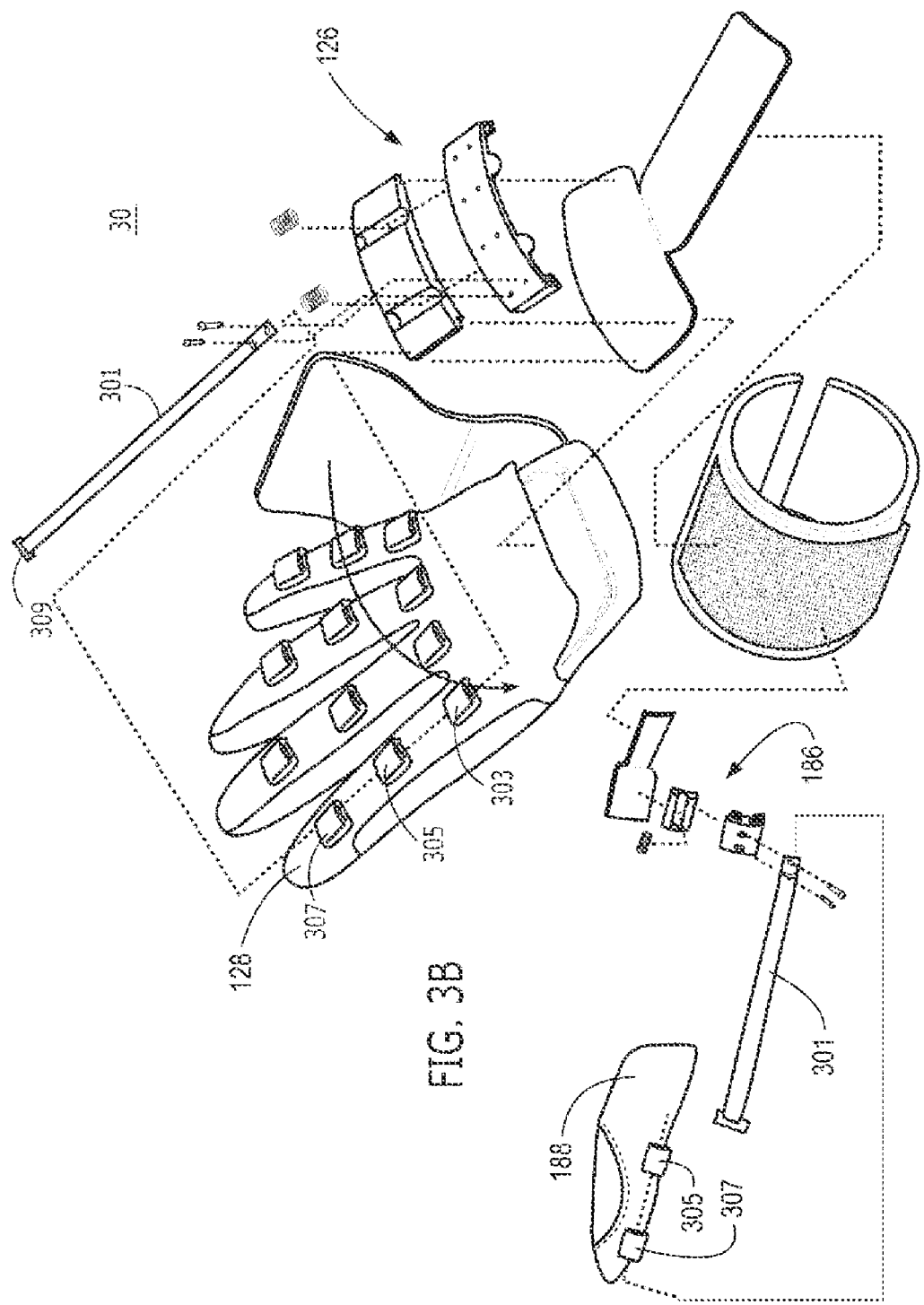

DYNAMIC HAND SPLINTS

CLAIM OF PRIORITY

The present application is a continuation of U.S. patent application Ser. No. 11/164,954, filed Dec. 12, 2005, now U.S. Pat. No. 7,892,194, which is a non-provisional patent application of, and claims priority under 35 U.S.C. §119(e) to, U.S. Provisional Patent Application Ser. No. 60/635,332, filed Dec. 10, 2004, the entire disclosures of which are incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

FIELD OF THE INVENTION

The present invention generally relates to orthoses and, in particular, to dynamic hand splints.

BACKGROUND OF THE INVENTION

Many people suffering a neurological injury from stroke, cerebral palsy, brain injury, etc., have upper extremity impairments. Many have some shoulder and elbow movements, but are unable to extend their wrist or fingers to grasp an object. This is usually due to hypertonicity, described in U.S. Pat. No. 5,807,293 as a condition where the flexor or extensor muscles in the upper extremities are spastic and resist positioning Dynamic splints can be used to offer slight resistance to hold joints in certain positions. An effective dynamic splint designed to be used for hypertonicity must offer enough force to balance the effects of the increased muscle tone. Such a dynamic splint is disclosed and described, for example, in United States Patent Application Publication No. US2003/10162634 to Farrell et al. Embodiments of the present invention present yet additional, alternative designs for a dynamic splint.

SUMMARY OF THE INVENTION

The present invention includes many aspects and features. Moreover, while many aspects and features relate to dynamic hand splints and orthoses, and are described in detail with respect to preferred embodiments illustrated in the drawings, the present invention is not limited to such preferred embodiments.

A dynamic hand splint includes as elements thereof: a forearm support section and a hand support section that are configured to be releasably attached to a forearm; and one or more finger tensioners that are releasably attached to the hand support section and that are configured to be releasably attached to a respective finger such that, when the finger is flexed from an extended position toward a flexed position, the finger is urged by the finger tensioner toward an extended position.

In a feature of the invention, each finger tensioner is semi rigid and extends outwardly from the hand support section in a direction away from the forearm support section.

In another feature, each finger tensioner comprises a resilient strut and includes a strap proximate a distal end thereof that is dimensioned and configured to wrap about a distal end of a respective finger to which the finger tensioner is to be attached. The strut may comprise a resilient rod or a strip of spring steel.

In a feature of the invention, the finger tensioners comprise resilient struts having varying degrees of resistance.

In another feature, the dynamic hand splint further includes a finger sleeve having a pocket in which a finger tensioner extends. The pocket preferably is configured to extend along a dorsal side of the sleeve, and the finger tensioner preferably comprises a resilient rod or a strip of spring steel.

In still yet another feature, the finger tensioner comprises a resilient band that is threaded through a plurality of raised guides that are secured to a respective digit sleeve. The finger tensioner preferably is threaded through the guides from the distal portion of the digit sleeve to the proximal portion of the distal sleeve and includes a stop or cap for engaging the distal guide to keep the band from being completely pulled through the distal guide. The guides are raised and serve to support the band at a point above the sleeves and out of abutment with one or more joints of the digits, especially during flexion of the finger.

In a feature of the invention, the forearm support section comprises a flexible tubular member that is dimensioned and configured to surround and provide a friction, interference fit on a forearm. The forearm support section may comprise a strap configured to be wrapped about said flexible tubular member to secure the forearm support section to the forearm, with the strap including hook-and-loop type elements for engaging corresponding hook-and-loop type elements on an outer surface of the flexible tubular member. Additionally, the hook-and-loop type elements on the outer surface of the flexible tubular member preferably are integrally formed as part of the flexible tubular member during an injection molding process. The hand support section also may include an area of hook-and-loop type elements on a volar side of a base thereof and the forearm support section may include an area of mating hook-and-loop type elements on a dorsal side thereof, wherein the hand support section and the forearm support section comprise non-integral pieces releasably attached together.

In a feature of the invention, the forearm support section comprises a malleable material and includes a bend therein, whereby the forearm support section is configured to determine an angle at which a wrist will be disposed relative to a forearm when the forearm support section is donned.

In still yet another feature, each finger tensioner is pivotally mounted to the hand support section for rotational (adductional and abductional) movement relative to the hand support section, whereby the finger tensioners may be splayed. Once properly oriented, a screw can be tightened to lock the tensioner in the desired orientation.

Each finger tensioner also may be mounted to the hand support section through a member that is mounted to the hand support section for sliding movement relative thereto, in accordance with still yet another feature. In this respect, each finger tensioner preferably is thereby linearly movable relative to the hand support section to allow the finger tensioners to travel with and remain positioned over the respective finger throughout flexion and extension. The member preferably slides on a housing and the housing preferably includes a compression spring that is configured to collectively urge the finger tensioners toward the housing upon flexing of the fingers to which the finger tensioners are attached. Alternatively, a compression spring could be configured to urge a single finger tensioner toward the housing upon flexing of the finger to which the finger tensioner is attached.

In still yet another feature, the dynamic hand splint additionally includes: a thumb support section releasably attached to the forearm support section; and a thumb tensioner releasably attached to the thumb support section and configured to be releasably attached to a thumb such that, when the thumb is flexed from an extended position toward a flexed position, the thumb is urged by the thumb tensioner toward an extended position. With respect to this feature, actuation of the thumb tensioner preferably does not actuate a finger tensioner (i.e., they are not interconnected to move together). Similarly, actuation of a finger tensioner does not actuate the thumb tensioner.

In another feature of the invention, the forearm support section includes an interior surface comprising a removable padded lining. The lining further may include a non-skid material in order to prevent distal migration of said forearm support section. The same or a similar non-skid material may be included on the volar sides of digit sleeves and/or on a palm covering to assist in gripping of an object by the hand using the dynamic hand splint.

In still yet another feature, the hand support section includes, on a dorsal side thereof, quick-release attachment sites for changing of the finger tensioners releasably attached to the hand support section. By changing of the finger tensioners, differing resistances to the flexing of the fingers can readily and easily be provided.

Another aspect of the invention includes a method for donning elements of a dynamic hand splint, comprising the steps of: attaching a forearm support section and a hand support section to a forearm; attaching finger tensioners to the hand support section; and attaching each of the finger tensioners to a respective finger such that, when the finger is flexed from an extended position toward a flexed position, the finger is urged by the finger tensioner toward an extended position.

In accordance with a feature of this aspect, each of the finger tensioners extends between the finger to which it is attached and the hand support section.

In another feature, the step of attaching each of the finger tensioners to a respective finger comprises strapping a distal end of a resilient strut to a distal end of the respective finger. Preferably, the strut comprises a resilient rod or a strip of spring steel.

In still yet another feature, the step of attaching each of the finger tensioners to a respective finger comprises inserting a resilient strut into a pocket of a sleeve in which the respective finger is disposed. Preferably a finger tensioner is secured to a dorsal side of a respective finger, and the finger tensioner comprises a resilient rod or a strip of spring steel.

In another feature, the step of attaching each of the finger tensioners to a respective finger comprises threading a resilient band through a plurality of guides that are secured to a sleeve in which a respective digit is disposed. The guides preferably are secured to a dorsal side of the respective digit, with a guide being disposed on each phalanx of the digit.

In another feature, the step of attaching finger tensioners to the hand support section comprises attaching finger tensioners to the hand support section at the base of the respective finger proximate the dorsum of the hand, each finger tensioner extending only between such point of attachment to the hand support section and the distal end of the respective finger to which the finger tensioner is attached.

In another feature, the step of attaching a forearm support section and a hand support section to a forearm comprises the step of partially encircling a forearm with a flexible tubular member that is dimensioned to provide a friction, interference fit on the forearm. In this regard, the method may further comprise the step of fastening a strap about the flexible tubular member to secure the forearm support section to the forearm, the strap including hook-and-loop type elements for engaging corresponding hook-and-loop type elements on the outer surface of the flexible tubular member. The hook-and-loop type elements on the outer surface of the flexible tubular member also may be integrally formed with the flexible tubular member during an injection molding process. The step of attaching a support comprising a forearm support section and a hand support section to a forearm also may comprise engaging an area of hook-and-loop type elements on a volar side of a base of the hand support section to an area of hook-and-loop type elements on a dorsal side of the forearm support section, wherein the hand support section and the forearm support section comprise non-integral pieces. In this respect, the hook-and-loop fasteners connect together the forearm support section and the hand support section. The method also may further comprise the step of fastening a strap about the flexible tubular member and the base of the hand support section thereby securing the hand support section to the forearm support section, the strap including hook-and-loop type elements for engaging corresponding hook-and-loop type elements on the outer surface of the flexible tubular member.

In still yet another feature, the step of attaching a forearm support section and a hand support section to a forearm comprises the steps of wrapping a strap about the forearm and attaching opposite ends of the strap to the forearm support section, the hand support section and the forearm support section being integral and forming a single element of the dynamic hand splint. The forearm support section and the hand support section may be integrally formed together in an injection molding process in this regard.

In another feature of the invention, the method further includes the step of bending the hand support section prior to attaching the hand support section to the forearm support section in order to determine the angle at which the wrist will be disposed to the forearm, the step of attaching the hand support section to the forearm support section including positioning of the bend in the hand support section proximate the wrist.

In another feature, the hand support section extends between the dorsum of the hand proximate the base of the fingers to only a few inches past the wrist along the forearm.

In still yet another feature, the step of attaching finger tensioners to the hand support section includes orienting each finger tensioner about an axis that is generally orthogonal to the ulnar-radial plane whereby adjacent fingers are splayed in the ulnar and/or radial direction.

In an additional feature, the step of attaching finger tensioners to the hand support section includes attaching the finger tensioner to a member that is mounted to the hand support section for sliding movement relative thereto.

In still another feature, the method further includes the steps of: attaching a thumb support section to the forearm support section; attaching a thumb tensioner to the thumb support section; and attaching the thumb tensioner to a thumb such that, when the thumb is flexed from an extended position toward a flexed position, the thumb is urged by the thumb tensioner toward an extended position. In this regard, the thumb preferably is urged toward an extended position independent of any urging of a finger toward an extended position by a finger tensioner. Also, a finger preferably is urged toward an extended position independent of any urging of the thumb toward an extended position by the thumb tensioner.

In still yet another feature, the method includes the additional steps of: detaching each of the finger tensioners from the respective finger; and detaching the finger tensioners from the hand support section. The method also may include the steps of: attaching a thumb support section to the forearm support section; attaching a thumb tensioner to the thumb support section; and attaching the thumb tensioner to a thumb such that, when the thumb is flexed from an extended position toward a flexed position, the thumb is urged by the thumb tensioner toward an extended position independent of any finger tensioners, the finger tensioners having previously been detached. Thereafter, the method may include the steps of: detaching the thumb tensioner from the thumb; detaching the thumb tensioner from the thumb support section; detaching the thumb support section from the forearm support section; and detaching the forearm support section from the forearm.

In another aspect, a method for donning elements of a dynamic hand splint by a patient includes the steps of: attaching a forearm support section to a forearm; next, attaching the digit tensioners to respective digits (fingers and/or thumb), the digit tensioners being releasably attached to a hand support section; and next, attaching the hand support section to the forearm support section, wherein, when the digits are flexed from an extended position toward a flexed position, the digits are urged by the tensioners toward an extended position.

In a feature of this aspect, the hand support section is semirigid and the step of attaching the hand support section to the forearm support section comprises pivoting of the hand support section about the wrist into engagement with the forearm support section with the tensioners already attached to the digits.

In addition to the aforementioned aspects and features of the present invention, it should be noted that the present invention further includes the various possible combinations of such aspects and features. Examples of such combinations are illustrated in the detailed description set forth below.

BRIEF DESCRIPTION OF THE DRAWINGS

One or more preferred embodiments of the present invention now will be described in detail with reference to the accompanying drawings, which are for the purpose only of illustrating embodiments of the invention and are not intended to be to scale:

FIG. 3B is an exploded perspective view of the dynamic splint of FIG. 3A.

DETAILED DESCRIPTION OF THE INVENTION

Figure 1A:
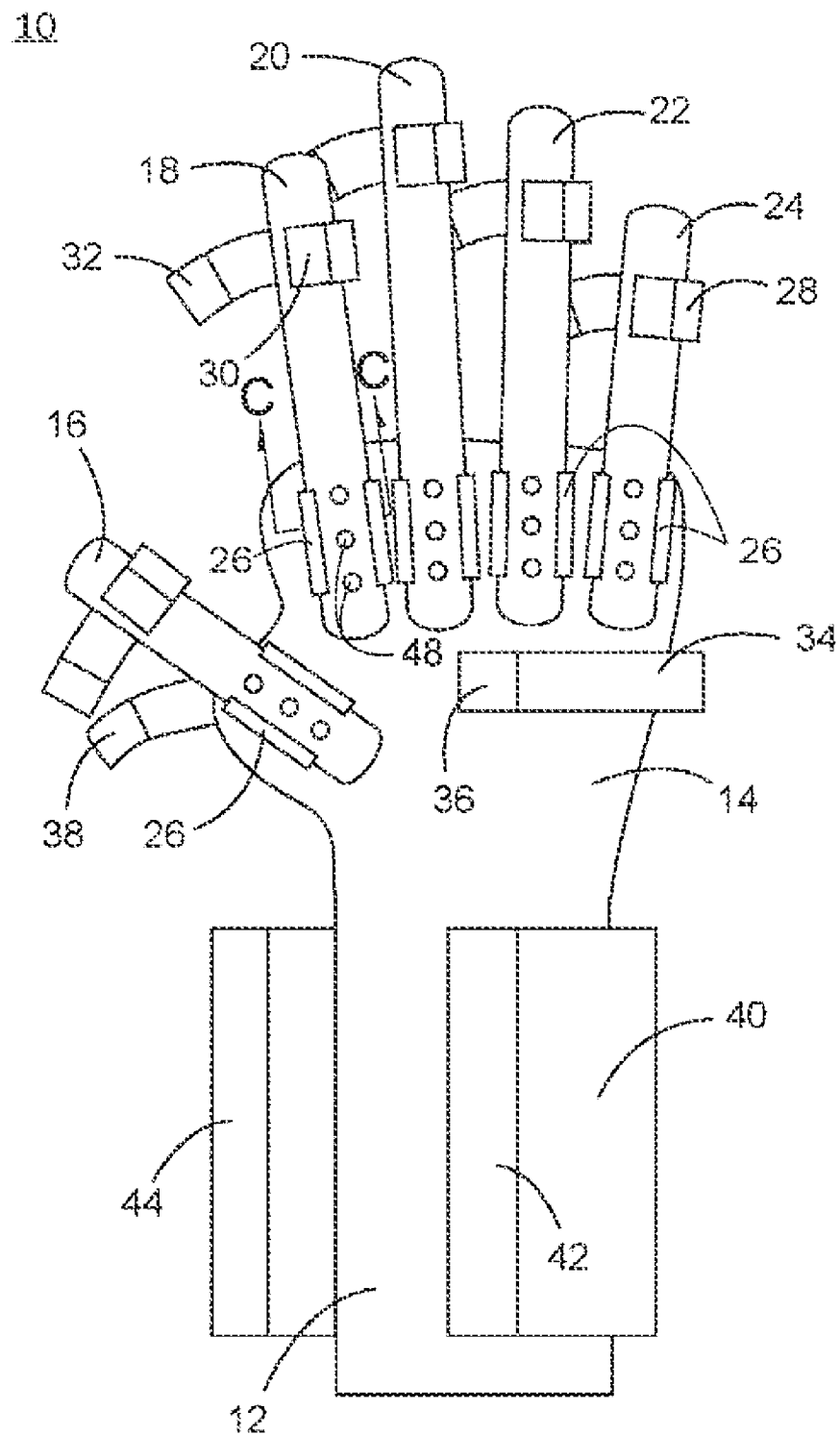
FIG. 1A is a top view of a dynamic splint in accordance with a first preferred embodiment of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at lease one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Additionally, several terms such as "dorsal," "volar," "radial," and "ulnar" are used herein with reference to features of the human hand. Indeed, descriptions herein of one or more illustrated embodiments of the invention sometimes are made with such terms that may imply that the embodiment is disposed on a forearm and hand. Use of such terms of reference is made herein in order to facilitate an understanding of the invention, and the forearm and the hand are not considered in such embodiments to be actual elements of the invention.

Moreover, for the purpose of interpreting these terms of reference, the reader should consider a forearm and open hand resting palm-side down upon a planar desktop, with the forearm and palm generally contacting the desktop, and with the fingers and thumb generally straight and resting their lengths on the desktop. The volar sides of the forearm, wrist, hand, and fingers are generally disposed toward and contact the desktop. Thus, the fingerprints generally are found on the volar sides of fingertips. The dorsal sides of the forearm, wrist, hand, and fingers generally face in opposite direction to the volar sides of the forearm, wrist, hand, and fingers. These dorsal sides thus would be generally oriented away from the desktop. For example, fingernails generally grow from the dorsal sides of the fingers. The side of the hand from which the thumb depends defines the radial side of the forearm, wrist, and hand. In contrast, the side of the hand opposing the radial side defines the ulnar side of the forearm, wrist, and hand. For example, the fourth finger from the thumb of the hand, generally the smallest finger often called the "pinkie" finger, depends from the ulnar side of the hand. In view of these clarifications, these terms of reference are unambiguous and are well-defined with regard to essentially any hand or wrist, including both the left hand and right hand.

Regarding the views of the figures, dorsal views herein refer to views directed toward dorsal sides. For example, a dorsal view of a hand shows the dorsal side of the hand, which side is sometimes called the back of the hand. Similarly, a radial view of a hand generally would include a showing of the thumb, a volar view of a hand generally would include a showing of the palm, and an ulnar view of a hand generally would include a showing of the fourth finger from the thumb.

Regarding planes and axes, volar-dorsal planes are generally perpendicular to radial-ulnar planes, and the forearm generally defines a longitudinal axis. The reader should consider again the forearm and hand resting palm-side down on a planar desktop, particularly when the hand and forearm are comfortably aligned and the fingers are extended straight and held tightly together. In this disposition of the forearm and hand, the plane of the desktop defines a radial-ulnar plane; a longitudinal axis is defined along the length of the forearm; and the four fingers of the hand extend generally parallel to the longitudinal axis. Furthermore, rotation of a radial-ulnar plane by ninety degrees about the longitudinal axis produces a volar-dorsal plane. For example, when a postcard is slipped between adjacent fingers such that an edge of the postcard abuts the desktop and is held parallel to the longitudinal axis, and such that the postcard stands vertically and ninety degrees from the plane of the desktop, the postcard defines a volar-dorsal plane.

Furthermore, terms of reference such as "phalanx," "phalange," and "interphalangeal joint," which terms are well-known and are found in the prior art, may be used herein with reference to the skeletal anatomy of the human hand. Indeed, descriptions herein of one or more illustrated embodiments of the invention sometimes are made with such terms that may imply that the embodiment is disposed on or abuts the hand. Use of such terms of reference is made herein in order to facilitate an understanding of the invention while the hand and portions thereof are not necessarily considered in such embodiments to be actual elements of the invention.

Nonetheless, for the purpose of interpreting these terms of reference, reference is herein made to the fourth figure of U.S. Pat. No. 5,676,157 to Kramer, which issued on Oct. 14, 1997 (the "Kramer patent"). In the fourth figure of the Kramer patent, which figure is hereby incorporated herein by reference, the skeletal anatomy of a human hand is illustrated wherein particular bones and joints defined therebetween are identified. For the purpose of interpreting terms of reference as used herein, the fourth figure of the Kramer patent may be regarded as a dorsal view of a right hand. As shown and as is commonly known, five digits, including a thumb and four fingers, depend from the hand. The three bones of any one of the four fingers, disposed in increasing distance from the hand, are referred to as: the proximal phalange (or proximal phalanx); the middle phalange (or middle phalanx); and the distal phalange (or distal phalanx). A section of a finger may be referred to herein with regard to a particular phalange without ambiguity in that such a section would include the particular bony phalange and the flesh of the finger about the phalange. For example, in typing or in entering data using a keyboard, distal phalange sections of the fingers generally abut and actuate keys of the keyboard without regard to whether distal phalange bones, which are generally surrounded by the flesh of the fingers, ever directly contact the keyboard.

With regard to joints, for each of the four fingers illustrated in the fourth figure of the Kramer patent, a proximal interphalangeal joint is defined between the proximal phalange and the middle phalange, and a distal interphalangeal joint is defined between the middle phalange and the distal phalange. The thumb, however, having less joints than each of the four fingers, generally includes an interphalangeal joint, indicated in the fourth figure as "THUMB IP," defined between a proximal phalange (or proximal phalanx) and a distal phalange (or distal phalanx). Thus, any recitation herein relating to the "last joint" or "distal joint" of a digit relates equally to any distal interphalangeal joint of a finger and to any interphalangeal joint of a thumb regarding either a left hand or a right hand.

Turning now to the drawings of the present application, preferred embodiments of a dynamic hand splint of the present invention are illustrated and are described in detail below. It should be furthermore understood that the views found in the accompanying drawings relate to a dynamic hand splint for a right forearm, wrist, and hand. Nevertheless, the accompanying drawings and the descriptions herein relate equally as well to a dynamic hand splint for a left forearm, wrist, and hand when a mirror image of the various drawings is considered.

Each preferred embodiment comprises a dynamic splint for the positioning and exercise of a neurologically impaired upper extremity, including the wrist, hand, and fingers, and is specifically directed towards a dynamic splint that exercises a rehabilitating hand by providing resistance to the hand's fingers and thumb. Each of these embodiments is especially useful for returning the fingers and thumb to an open or extended position after a grasping motion has been carried out and, specifically, is used to hold the user's impaired wrist, hand and fingers generally in an extended position, with the thumb in palmer abduction. This position places the impaired hand in the functional position for grasping. Each embodiment thus allows a neurologically impaired upper extremity, including the hand, to work on repetitive grasp-and-release activities while participating in task-specific arm training Each embodiment further has a dynamic characteristic that offers varying degrees of substantial resistance to the digits.

The First Embodiment

Figure 1B:
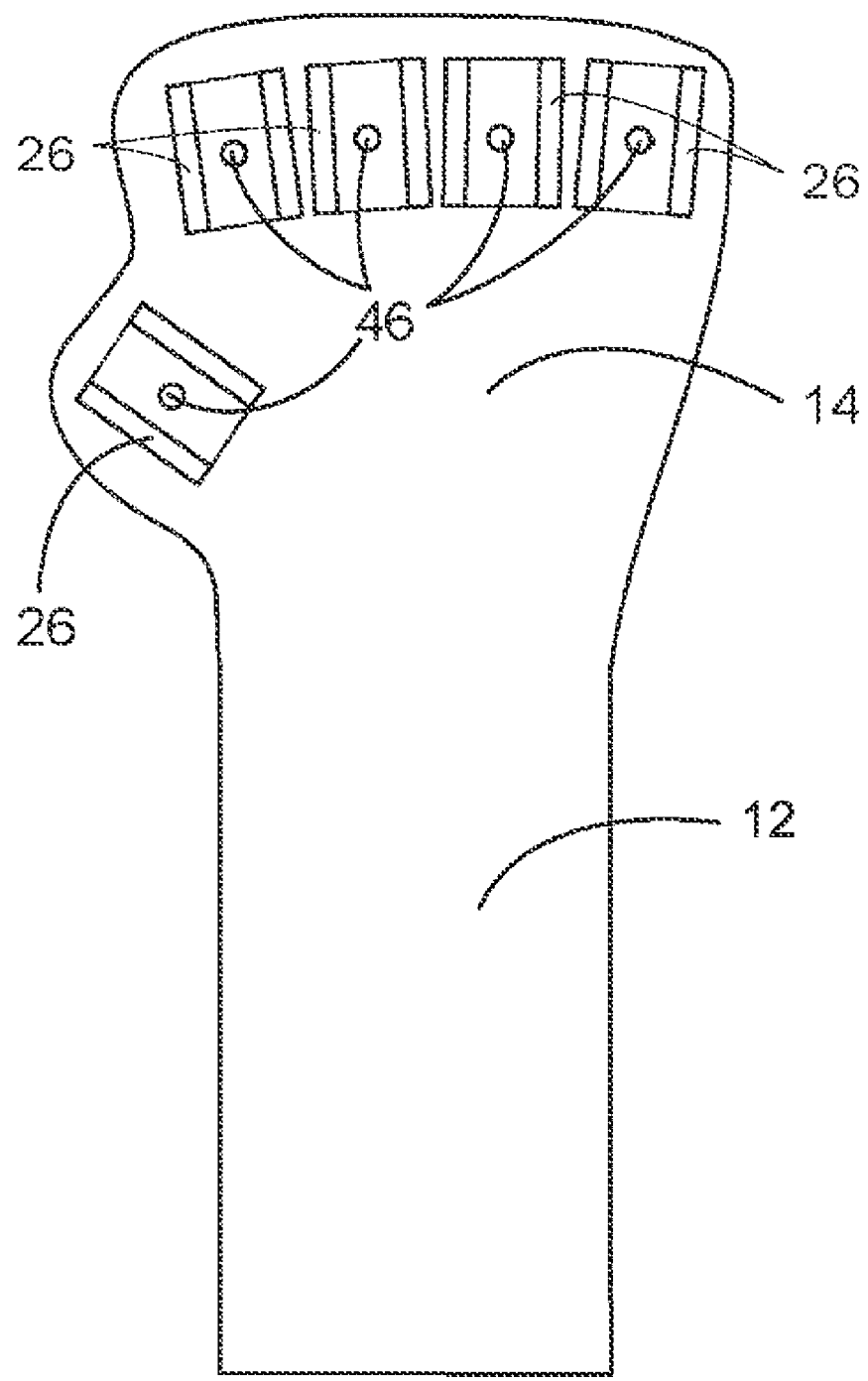
FIG. 1B is a top view of the hand and forearm support sections and clips of the dynamic splint of FIG. 1A.
Figure 1C:
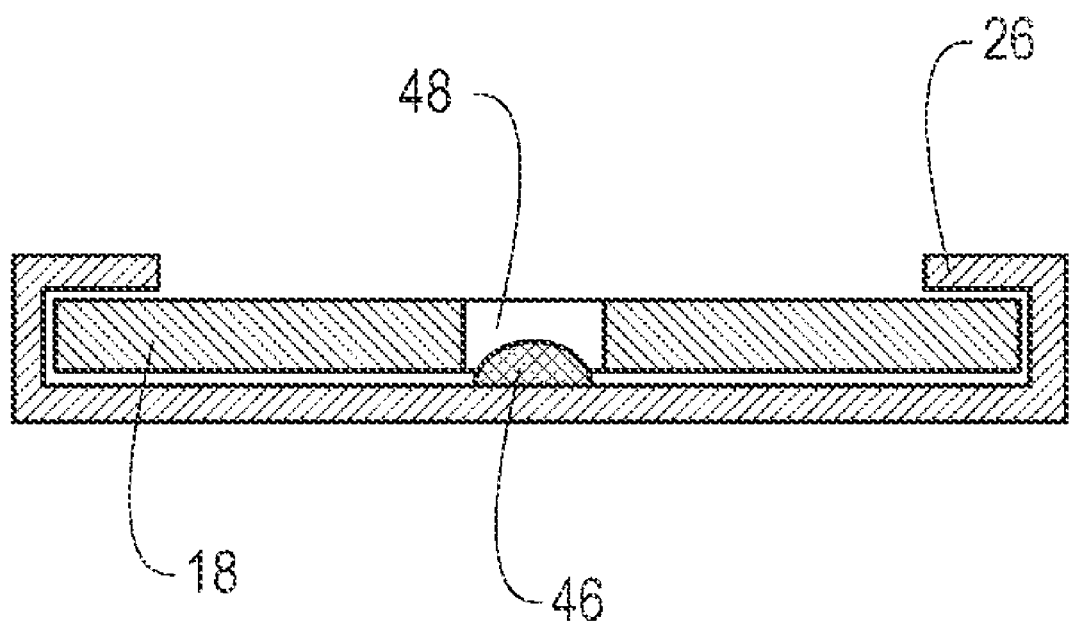
FIG. 1C is a cross-sectional view of a strut and clip of the dynamic splint of FIG. 1A, taken along line C-C.

A dynamic hand splint 10 in accordance with a first preferred embodiment of the present invention is illustrated in FIGS. 1A-1C. The splint 10 includes a forearm support section 12 and a hand support section 14. As shown, the forearm support section 12 and the hand support section 14 (including both the portions, described below, that are related to the fingers and to the thumb) are integrally formed and together constitute a component of the dynamic hand splint. Alternatively, however, the forearm support section 12 and the hand support section 14 are not integral but, instead, are attached together directly or indirectly through an intermediate connector such as hook-and-loop fasteners (of which the second and third embodiments disclosed below are exemplary). Also alternatively, the portion of the hand support section 14 that is related to the fingers and the portion of the hand support section 14 that is related to the thumb are not integral but, instead, are separately attached to the forearm support section 12 (of which the second and third embodiments discussed below are likewise exemplary).

Both the forearm support section 12 and the hand support section 14 are constructed of a pliable, malleable material, e.g., a plastic or metal sheet that can be readily manipulated and shaped by a healthcare professional. In this regard, the forearm support section 12 preferably can be bent upward or downward, as desired, in the area of the wrist in order to position the wrist at a selected one of a wide variety of angles when the dynamic splint is used. In use, the forearm support section 12 is adjusted so that the hand support section 14 is positioned at an upward angle to the forearm support section 12 so that the wrist is positioned upwardly (which angle is exemplified by the second and third embodiments disclosed below). Similarly, the hand support section 14 preferably can be bent in an arch in order to support and maintain a particular palmer arch of a hand.

The forearm support section 12 itself is configured and dimensioned to extend along a forearm from the wrist rearwardly preferably about five inches. The forearm support section 12 also preferably includes one or more straps for securing the forearm support section 12 in proper disposition to the forearm. Such straps may include hook-and-loop fasteners such as VELCRO® fasteners. Alternatively, the forearm section 12 is configured to cover the dorsal side of the forearm and may substantially encircle the forearm to provide a friction, interference fit with the forearm (of which configuration the second and third embodiments disclosed below are exemplary).

As illustrated, a releasable fastener such as a strap 40 has a first end attached to the dorsal side of the forearm support section 12. The strap 40 includes an area 42 of loops proximate its first end, and the strap 40 includes a second end having an area 44 with mating hooks for hook-and-loop engagement with the area 42 of loops. In this respect, the strap 40 includes a length that is sufficient to wrap around the forearm to effect the hook-and-loop engagement. The inner surface of the forearm support section 12 further is preferably lined with a padding material (not shown) for comfort.

The hand support section 14 is dimensioned and configured to cover a substantial portion of the dorsal part or dorsum of the hand between the metacarpophalangeal joints and the carpals, i.e., between the base of the fingers and the wrist. The hand support section 14 also preferably includes one or more straps for securing the hand support section 14 in proper disposition on the back of the hand. Such straps may include hook-and-loop fasteners such as VELCRO® fasteners.

As illustrated, a releasable fastener such as a strap 34 has a first end attached to the dorsal side of the hand support section 14. The strap 34 includes an area 36 of loops proximate its first end, and the strap 34 includes a second end having an area 38 with mating hooks for hook-and-loop engagement with the area 36 of loops. In this respect, the strap 34 includes a length that is sufficient to wrap around the palm of the hand to effect the hook-and-loop engagement. The inner (volar) surface of the hand support section 14 further is preferably lined with a padding material (not shown) for comfort.

The first embodiment 10 additionally includes tensioners comprising a plurality of struts 18,20,22,24 for attachment to respective fingers of the hand. Each strut 18,20,22,24 furthermore is preferably constructed from a resilient material and is approximately the length and width of the digit to which it is to be attached.

Suitable struts may comprise, for example, resilient strips of about 0.01- to 0.008-inch stainless steel that are semi-rigid but nevertheless exhibit spring-like qualities and that may be generally rectangular in cross-section. Alternatively, the struts may be circular or oval in cross-section and comprise rods. Semi-rigid, resilient rods are conventional and are disclosed, for example, in U.S. Pat. No. 5,453,064 to Williams, Jr. (the "Williams patent").

Such rods as disclosed in the Williams patent are made of a material such as a composite and can be formed from a hardenable mixture of filaments or fibers saturated in a resin system, or can be made of any other resilient material with a suitable toughness to give a useful flexural fatigue life, such as advanced composite thermoplastics, thermosets, engineered plastics, or fiber reinforced plastics. The preferred rods of the Williams patent are formed from Owens-Corning S2-glass with a matrix material of an epoxy or a resin and comprise about 65 to about 70 volume percent S2-glass in an epoxy matrix, giving the rods an appropriate desired flexural strength.

Each of the struts 18,20,22,24 is configured at a distal end thereof to be secured to a distal portion of a respective finger of the hand. As illustrated, each strut 18,20,22,24 includes a releasable fastener comprising a strap 28 having a first end attached to the dorsal side of the respective strut 18,20,22,24. Each strap 28 includes an area 30 of loops proximate its first end, and the strap 30 includes a second end having an area 32 with mating hooks for hook-and-loop engagement with the area 30 of loops. In this respect, the strap 28 is of a length that is sufficient to wrap around the respective finger of the hand to effect the hook-and-loop engagement. The inner surface of the strut 18,20,22,24 further is preferably lined with a padding material (not shown) for comfort.

Each strut 18,20,22,24 is also releasably attached to the hand support section 14 by a respective clip 26 mounted on the dorsal side of the hand support section 14. As illustrated, the hand support section 14 includes four such clips 26 into which the proximal ends of the struts 18,20,22,24 are inserted. Each attachment clip 26, illustrated in greater detail in FIG. 1C, includes a channel formed by facing C-sections and a detent 46 that extends upwardly from the floor of the channel. Each strut 18,20,22,24—exemplified by strut 18 in FIG. 1C—includes a plurality of axially aligned openings 48 selectively mateable with the detent 46 to secure and lock the strut 18,20,22,24 within the channel The detent 46 further is selectively displaceable, whereby the strut 18,20,22,24 may be linearly retracted or extended relative to the hand support section 14 to adjust for the length of a particular finger. Furthermore, the cross-section of each clip 26 is shaped and dimensioned such that the channel created thereby has approximately the cross-sectional shape of the strut 18,20,22, 24, thereby minimizing any play that otherwise might be exhibited by the strut 18,20,22,24 when secured within the channel by the protuberance 46. Alternatively, in an arrangement not illustrated herein, the strut 18,20,22,24 may include a detent that is selectively insertable into one of a plurality of openings in the bottom of the channel As illustrated, the hand support section 14 also includes a tensioner comprising strut 16 for attachment to a thumb. The thumb strut 16 is similar to each of the finger struts 18,20,22, 24. The thumb strut 16 is preferably also constructed from a resilient material and is approximately the length of the thumb to which it is to be attached. A suitable strut may comprise, for example, a thin resilient strip of about 0.01- to 0.008-inch stainless steel that is semi-rigid but nevertheless exhibits spring-like qualities.

The thumb strut 16 also is configured at a distal end thereof to be secured to a distal portion of the thumb. As illustrated, the strut 16 includes a releasable fastener comprising a strap 28 having a first end attached to the dorsal side of the strut 16. Like the straps 28 used for the finger struts 18,20,22,24, this strap 28 includes an area 30 of loops proximate its first end, and the strap 28 includes a second end having an area 32 with mating hooks for hook-and-loop engagement with the area 30 of loops. In this respect, the strap 28 is of a length that is sufficient to wrap around the thumb to effect the hook-and-loop engagement. The inner surface of the strut 16 further is preferably lined with a padding material (not shown) for comfort.

The thumb strut 16 is also releasably attached to the hand support section 14 by a clip 26 mounted on the dorsal side of the hand support section 14 in the same manner by which each of the finger struts 18,20,22,24 is mounted to a respective clip 26.

As will be appreciated by the Ordinary Artisan, while the preferred embodiment 10 of FIGS. 1A, 1B, and 1C includes struts 16,18,20,22,24 for all five digits, a dynamic hand splint alternatively may include only struts and associated clips for one or more fingers, for just the thumb, or for any of the possible combination of digits, as desired.

In use of the dynamic hand splint 10 of FIGS. 1A-1C, the forearm support section 12 and the hand support section 14 are shaped or adjusted as desired. In this respect, a healthcare worker, the wearer himself, or another user preferably shapes the support sections 12,14 by arching the hand support section 14 to accommodate the palmer arch of the hand of the wearer, and by bending the forearm section 12 to achieve the desired angle for positioning of the wrist of the wearer.

The struts 16,18,20,22,24 having the respective, desired resilience are inserted into the clips 26 at the appropriate lengths to match the lengths of the digits of the wearer. The forearm support section 12 and the hand support section 14 then are secured on the dorsal sides of the wearer's hand and forearm with respective straps 40,34, and each of the struts 16,18,20,22,24 are secured onto the digits of the hand with the strut straps 28.

Once attached, the dynamic splint 10 creates rearwardly-directed forces that urge the fingers and thumb into an open hand position in which the fingers and thumb are extended. However, the resistance provided by each of the digit tensioners, i.e., each of the struts 16,18,20,22,24 in the preferred embodiment 10, is not so great as to prevent the wearer from moving the fingers and thumb towards a gripping position, thereby allowing the wearer to exercise (and rehabilitate) the hand. Indeed, the dynamic splint 10 will generally position the wrist into extension with the digits extended, whereby the wearer will be in a position to grasp an object, and after the wearer grasps the object, the dynamic splint 10 then will assist in reopening of the digits so the wearer will once again be in a position to grasp an object. Furthermore, the struts 16,18,20,22,24 may be replaced by struts of different degrees of resilience, whereby the healthcare worker, the wearer or another user can continue to select struts with the desired resistance for each digit as the healing and rejuvenation process progresses.

The Second Embodiment

Figure 2A:
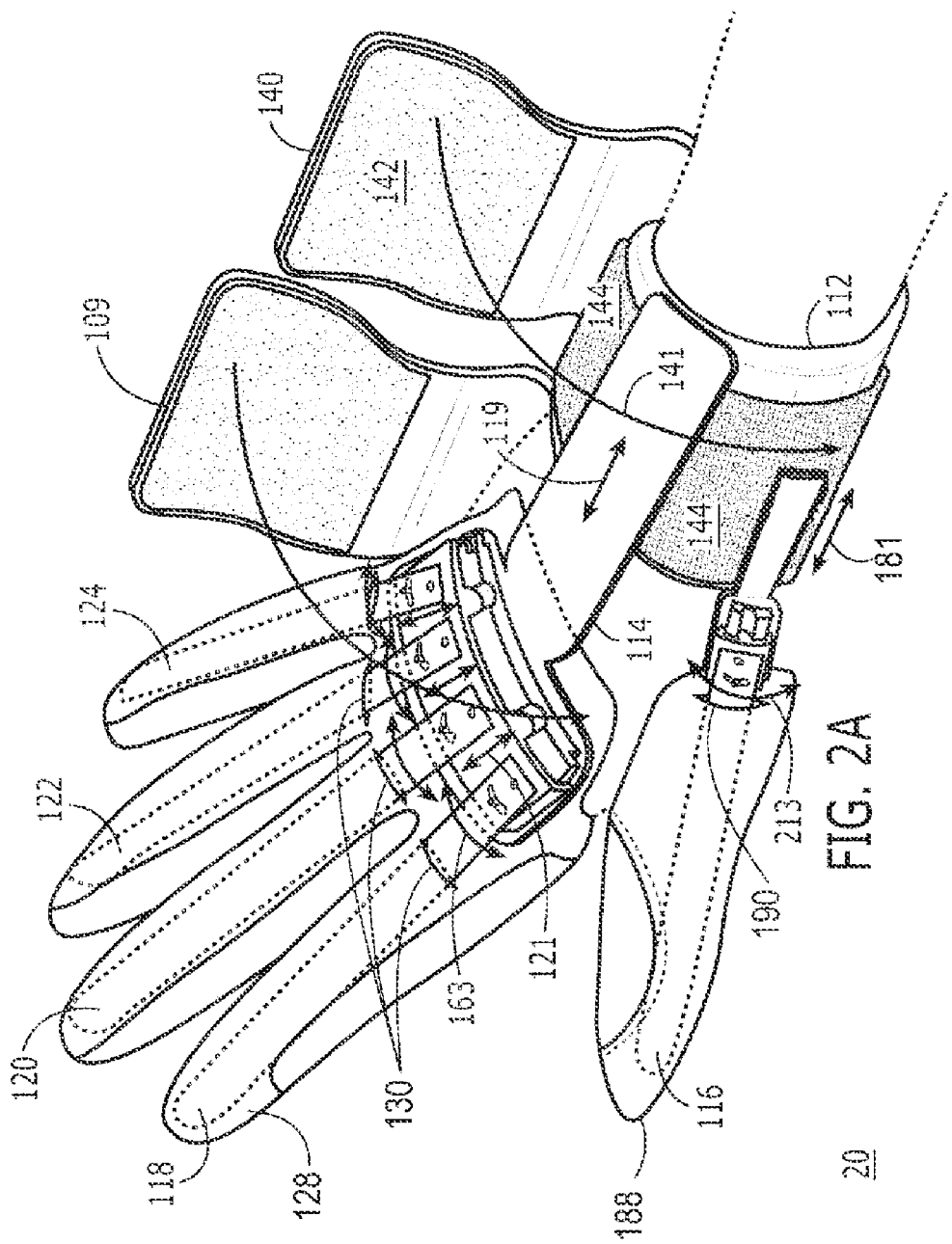
FIG. 2A is a perspective view of a dynamic splint in accordance with a second preferred embodiment of the present invention.
Figure 2B:
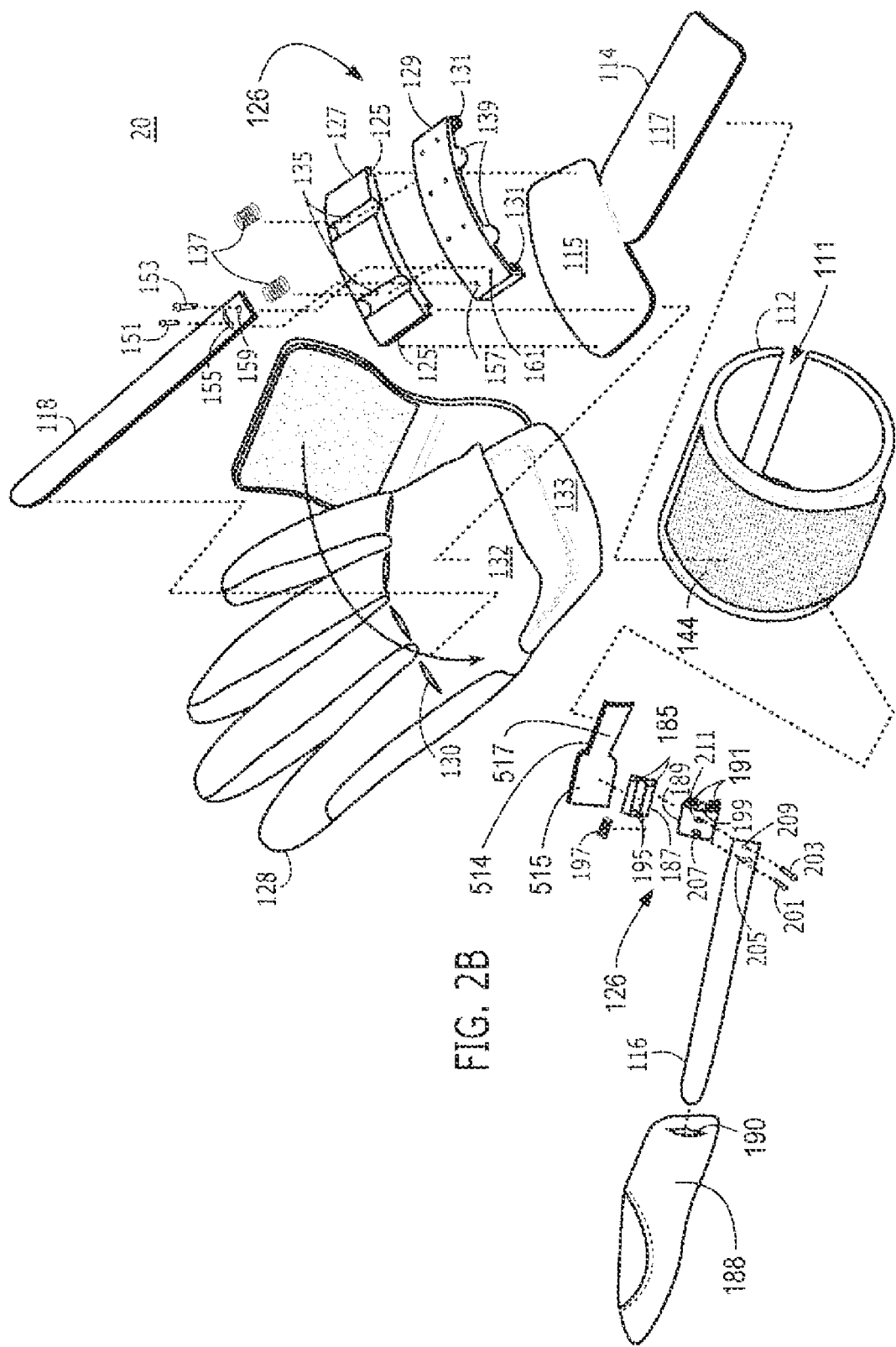
FIG. 2B is an exploded perspective view of the dynamic splint of FIG. 2A.

A dynamic hand splint 20 in accordance with a second preferred embodiment of the present invention is illustrated in FIGS. 2A and 2B. As with the splint 10 of FIGS. 1A-1C, this second splint 20 includes a forearm support section 112 and a hand support section 114. Unlike the forearm support section 12 and the hand support section 14 of the splint 10 of the first embodiment, however, the forearm support section 112 and the hand support section 114 of the splint 20 of the second embodiment are not integrally formed but, instead, comprise two separate components of the dynamic hand splint 20. As such, the forearm support section 112 may be separately donned prior to donning of the hand support section 114.

The forearm support section 112 of the splint 20 of the second embodiment is preferably flexible and may be constructed from any suitable plastic, metal, or alloy material. The forearm support section 112 also preferably is configured and dimensioned to extend along a forearm from the wrist rearwardly for a distance of at least several inches, and is generally tubular and designed to surround the wrist and a portion of the forearm. The forearm support section 112 may be donned and doffed through a small opening or slot 111 that extends the complete length of the forearm support section 112 along the ulnar side of the wrist and forearm.

The forearm support section 112 also preferably is lined with a permanent or removable close cell foam padded lining (not shown) and is adapted to tightly fit around the wrist and forearm in a frictional, interference fit. The lining optionally may include a non-skid material on the inner surface thereof to help prevent distal migration of the forearm support section 112.

Additionally, the forearm support section 112, when manufactured in an injection molding process, preferably includes an area 144 of hooks that is formed during the injection molding process as an integral part of the forearm support section 112. The area 144 of hooks preferably is adapted to attach to loops in conventional hook-and-loop attachment such as exemplified in VELCRO®-type attachments. Forming an area of hooks in an injection molded process is known and disclosed, for example, in U.S. Pat. No. 5,656,226 to McVicker.

The area 144 of hooks preferably is formed so as to substantially cover the outer surface of the forearm support section 112 extending between opposite ends thereof defining the slot 111 on the ulnar side of the forearm support section 112. The area 144 of hooks receives in hook-and-loop attachment areas of loops of a strap 140 of the forearm support section 112 (one such area 142 being shown in FIG. 2A). The strap 140 is used to further secure the forearm support section 112 in its proper disposition to the forearm when needed. The strap 140 is preferably dimensioned and configured to extend substantially around the forearm support section 112 in covering relation not only to the slot 111 of the forearm support section 112, but also to a base 117 of the hand support section 114. Disposition of such covering attachment of the strap 140 is illustrated by an arrow 141 in FIG. 2A. To facilitate this, the area 144 of hooks on the forearm support section 112 is also adapted to receive on the dorsal side thereof a plurality of loops (not shown) disposed on the underside of the hand support section 114 for removable attachment of the base 117 of the hand support section 114 to the forearm support section 112. In addition, the area 144 of hooks on the forearm support section 112 is adapted to receive on the radial side thereof another plurality of loops (not shown) disposed on the thumb strut 116 for removable attachment (indirectly) of the thumb strut 116 to the forearm support section 112. The base 117 and platform 115 elements of the hand support section 114 and the thumb strut 116 are described in further detail below.

The hand support section 114 covers a portion of the dorsum of the hand. In particular, the hand support section 114 includes a platform 115 that is dimensioned and configured to extend between the radial side of the hand proximate the index finger (sometimes referred to as digit #2) across the dorsum of the hand to the ulnar side of the hand proximate the little finger (sometimes referred to as digit #5), and between the metacarpophalangeal joints and the carpals, i.e., between the base of the fingers and the wrist. The hand support section 114 further includes a base 117 that is integral with the platform 115 and that is dimensioned and configured to extend from the wrist several inches up the wrist, but preferably does not extend past the distal end of the forearm support section 112, i.e., the end of the forearm support section 112 that is distal to the wrist.

The hand support section 114 preferably is constructed from a pliable, malleable material, e.g., a plastic or metal sheet that can be readily manipulated and shaped by a healthcare professional, the wearer, or another user. In this regard, the hand support section 114 preferably can be bent upward or downward at the juncture between the platform 115 and the base 117, as desired, such juncture being in the area of the wrist, in order to position the wrist at a selected one of a wide variety of angles when the dynamic splint 20 is used in order to accommodate wrist flexion and/or extension. Thus, in use, the hand support section 114 preferably is shaped so that the wrist is positioned upwardly as illustrated in FIG. 2A.

As alluded to previously, the hand support section 114, and specifically the base 117, preferably includes an area of loops (not shown) on the inner (volar) side of the hand support section 114 whereby the hand support section 114 is secured in proper disposition to the area 144 of hooks of the forearm support section 112. The base 117 of the hand support section 114 also may be lined in areas with a padding material (not shown) for comfort.

The dynamic splint 20 of the second embodiment additionally includes tensioners comprising a plurality of struts 118, 120,122,124 for attachment to respective fingers of the hand. Each strut 118,120,122,124 furthermore is preferably constructed from, for example, spring steel and is formed to have a thin or flat profile. The struts 118,120,122,124 further preferably are constructed to have varying degrees of resistance depending upon such factors as the thickness of the struts 118,120,122,124 and materials from which the struts 118, 120,122,124 are made. Different resistances may be preferred for use with fingers having different characteristics of overall tone, tissue softness, and length. Each strut 118,120,122,124 also preferably corresponds in length and width to the finger to which it is to be attached. Suitable struts 118,120,122,124 may comprise, for example, thin resilient strips of about 0.01 to 0.008 inch stainless steel that is semi-rigid but nevertheless exhibits spring-like qualities.

Each strut 118,120,122,124 is designed to be secured to a respective finger of the hand. As illustrated in FIGS. 2A and 2B, this is accomplished in the second dynamic splint 20 by insertion of each strut 118,120,122,124 in a respective elongate pocket 130, each elongate pocket 130 being disposed in a respective finger sleeve 128. The finger sleeves 128 resemble the finger sleeves of a glove and, preferably, are integrally formed. Each of the finger sleeves 128 further preferably is configured to enclose a respective one of the fingers, i.e., digit #2 through digit #5. The splint 20 of the second embodiment also preferably includes a covering 132 for part of the dorsum of the hand at the base of the fingers, which covering 132 also preferably is integrally formed, via conventional textile operation, with the finger sleeves 128. A similar covering 133 for the palm of the hand may be provided that is integral with the finger sleeves 128. The pocket 130 of each finger sleeve 128 similarly is preferably integrally formed with its respective finger sleeve 128 during a conventional textile operation.

The dorsum covering 132 preferably includes an area of loops (not shown) on the dorsal side thereof for attachment of the dorsum covering 132 to an area of hooks (not shown) of the platform 115 of the hand support section 114.

In an alternative construction not illustrated herein, the palm covering 133 may be omitted thereby providing for an open-palm construction, and each finger sleeve 128 may only cover the volar surface of the finger between the tip of the finger and the middle area of the proximal phalanx.

Each strut 118,120,122,124 preferably is releasably attached to the hand support section 114, and specifically to the platform 115 thereof, through an attachment mechanism 126, best illustrated in FIG. 2B, that is secured onto the dorsal side of the platform 115 of the hand support section 114. Specifically, the attachment mechanism 126 includes a housing 127, which is secured to the dorsal side of the platform 115 of the hand support section 114, and a slider 129, which mates with and slides, in directions designated by arrows 121 in FIG. 2A, on top of the housing 127. In this respect, the slider 129 includes a C-shaped channel 131 on opposite sides thereof that receive ledges 125 of the housing 127 in interlocking engagement. The housing 127 further includes grooves 135 in which springs 137 are received. The springs 137 abut the housing 127 and, when the slider 129 is in interlocking engagement with the housing 127, blocks 139 of the slider 129 engage the springs 137 and compress the springs 137 when the slider 129 moves away from the base 117. This compression occurs when the struts 118,120,122, 124 are extended during closing of the fingers, and the springs 137 assist in opening of the fingers by urging retraction of the struts 118,120,122,124, as described in detail below.

Each strut 118,120,122,124 is mounted to the slider by two fasteners preferably comprising screws 151,153. A first screw 151 extends through a curved slot 155 formed in the respective strut 118,120,122,124 and is received in mating engagement within a threaded opening 157 in the slider 129. A second screw 153 extends through a circular opening 159 formed in the respective strut 118,120,122,124 and is received in mating engagement within another threaded opening 161 in the slider 129. Due to this arrangement, each respective strut 118,120,122,124 is capable of rotational movement, in a respective direction designated by arrows 163, about its second screw 153, with its first screw 151, extending through its curved slot 155, acting as a stop defining the limits of such rotation. Moreover, either screw 151, 153 further may be tightened to lock the strut in a particular orientation.

As illustrated, the dynamic splint 20 of the second preferred embodiment also includes a tensioner comprising strut 116 for attachment to a thumb. The strut 116 furthermore is preferably constructed from, for example, spring steel and is formed to have a thin or flat profile. Suitable struts may comprise, for example, thin resilient strips of about 0.01 to 0.008 inch stainless steel that is semi-rigid but nevertheless exhibits spring-like qualities.

The thumb strut 116 further preferably corresponds in length and width to the thumb to which it is to be attached. The attachment is accomplished by insertion of the strut 116 into an elongate pocket 190 of a thumb sleeve 188. The thumb sleeve 188 preferably is configured to enclose a thumb, and the pocket 190 of the thumb sleeve 188 preferably is integrally formed in the thumb sleeve 188 in a textile operation.

The strut 116 preferably is releasably attached indirectly to the forearm support section 112 through a thumb support section 514 that, similar to the hand support section 114, includes a platform 515 and a base 517. In this respect, an attachment mechanism 186 is secured on the dorsal side of the platform 515 and functions to movably mount the strut 116 to the platform 515.

The base 517 of the thumb support section 514 includes an area of loops (not shown) on the volar side thereof for engagement with the area 144 of hooks on the forearm support section 112. The thumb support section 514, and in particular the base 517, preferably is configured and dimensioned such that, when it is worn, it includes a bend proximate the carpals of the wrist, spans the wrist joint, and preferably extends an inch or more along the forearm support section 112. Preferably the thumb support section 514 may thereby be selectively bent to various degrees of flexion and extension at the carpals in order to allow the thumb to be positioned in varying degrees of thumb abduction, adduction, and opposition, depending on where the attachment mechanism 186 is attached to the thumb support section 514.

With respect to the attachment mechanism 186, a slider 189 mates with and slides, in directions designated by arrows 181 in FIG. 2A, on top of the housing 187. In this respect, the slider 189 includes a C-shaped channel 191 on opposite sides thereof that receive side ledges 185 of the housing 187 in interlocking engagement, similar in manner to the housing 127 and slider 129 as discussed above.

Also in similar manner, the housing 187 further includes a groove 195 in which a spring 197 is received. The spring 197 abuts the housing 187 and, when the slider 189 is in interlocking engagement with the housing 187, a block 199 of the slider 189 engages the spring 197 and compresses the spring 197 when the slider 189 moves in a direction toward the thumb sleeve 188. This compression occurs when the strut 116 is extended during closing of the hand, and the spring 197 assists in opening of the hand by urging retraction of the strut 116 and extension of the thumb, as described in detail below.

The strut 116 is mounted to the slider 189 by two fasteners preferably comprising screws 201,203. A first screw 201 extends through a curved slot 205 formed in the strut 116 and is received in mating engagement within a threaded opening 207 in the slider 189. A second screw 203 extends through a circular opening 209 formed in the strut 116 and is received in mating engagement within another threaded opening 211 in the slider 189. Due to this arrangement, the strut 116 is capable of rotational movement, in the direction designated by the arrow 213, about the second screw 203, with the first screw 201, extending through the curved slot 205, acting as a stop defining the limits of such rotation.

As will be appreciated by the Ordinary Artisan, while the dynamic splint 20 of the preferred embodiment of FIGS. 2A and 2B includes struts 116,118,120,122,124 for all five digits, a dynamic hand splint alternatively may include only struts for one or more fingers, for just the thumb, or for any of the possible combination of digits, as desired.

Moreover, as will now be apparent, the strut 116 and attachment mechanism 186 for the thumb, as well as the thumb sleeve 188, may be separately and independently donned and doffed with respect to the struts 118,120,122,124 and attachment mechanisms 126 for the fingers, as well as the finger sleeves 128 and dorsum covering 132. Donning and doffing of a hand splint by a neurologically impaired or hemiparetic person can be problematic, especially when such a person only has the use of a single hand. Accordingly, the hand splint 20 of this second preferred embodiment (and the third preferred embodiment described below) is more readily donned and doffed by such a person.

In use of the dynamic hand splint 20 of this preferred embodiment, the forearm support section 112 is positioned onto the forearm. The hand support section 114 also is shaped as desired to position the wrist relative to the forearm. In this respect, a healthcare worker, the wearer himself, or another user preferably bends the hand support section 114 to achieve the desired angle for positioning of the wrist. The hand support section 114 is positioned or repositioned along the direction of arrows 119 on the forearm support section 112 such that the bend in the hand support section 114 is proximate to the wrist.

Struts 118,120,122,124 having the respective, desired resilience also are attached to the slider 129 via the screws 151,153; the slider 129 is engaged with the housing 127; the housing 127 is attached to the platform 115 of the hand support section 114; and the struts 118,120,122,124 are inserted into the pockets 130 of the respective finger sleeves 128 and each strut 118,120,122,124 is oriented in the desired rotational position. A strap 109 of the dorsum covering 132 (optionally provided) further may be fastened over the ends of the struts 118,120,122,124 and the attachment mechanism 126 for covering thereof. In this scenario, the strap 109 includes an area of loops (not shown) for engagement with areas of hooks (not shown) of the dorsum covering 132.

The strut 116 for the thumb also is shaped and manipulated to position the thumb relative to the forearm support section 112, and the strut 116 having the desired resilience is attached to the slider 189 via the screws 201,203; the slider 189 is engaged with the housing 187; the housing 187 is attached to the platform 515 of the thumb support section 514; and the strut 116 is inserted into the pocket 190 of the thumb sleeve 188 and is oriented in the desired rotational position. The strap 142, when provided, also preferably extends over and covers the base 517 of the thumb support section 514 including the attachment mechanism 186 in its disposition on the forearm support section 112.

Once attached, the dynamic splint 20 creates rearwardly-directed forces that urge the fingers and thumb into an open hand position in which the fingers and thumb are extended. However, the resistance provided by each of the digit tensioners, i.e., each of the struts 116,118,120,122,124 in the preferred embodiment 20, is not so great as to prevent the wearer from moving the fingers and thumb towards a gripping position, thereby allowing the wearer to exercise (and rehabilitate) the hand. Indeed, the preferred embodiment 20 will generally position the wrist into extension with the digits extended, whereby the wearer will be in a position to grasp an object and, after grasping of the object, the preferred embodiment 20 then will assist in reopening of the digits so the wearer will once again be in a position to grasp an object. Furthermore, each of the struts 116,118,120,122,124 may be replaced by struts of different degrees of resilience, whereby the healthcare worker, the wearer, or another user can continue to select struts with the desired resistance for each digit as the healing and rejuvenation process progresses.

The Third Embodiment

Figure 3A:
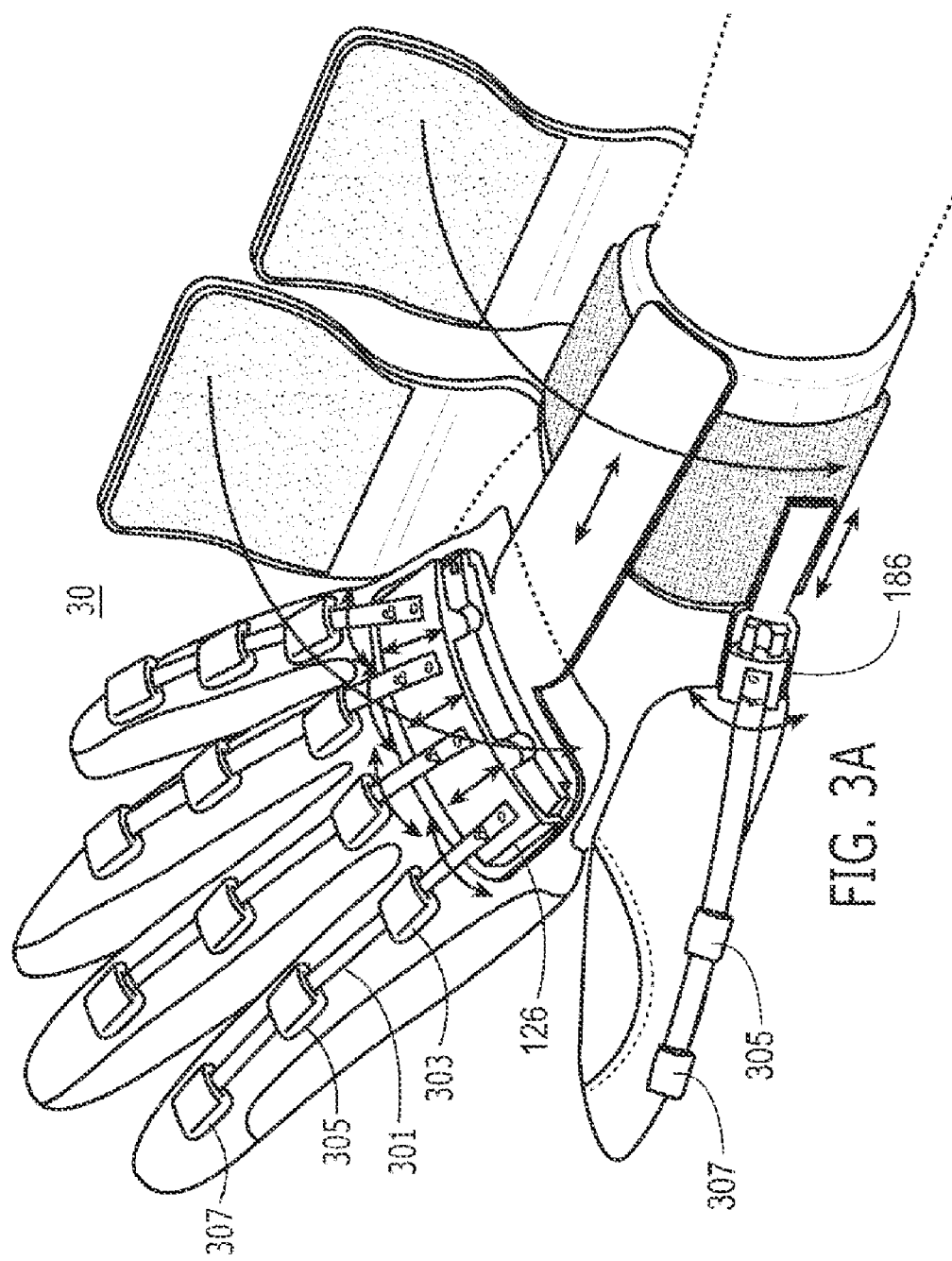
FIG. 3A is a perspective view of a dynamic splint in accordance with a third preferred embodiment of the present invention.

A dynamic hand splint 30 in accordance with a third preferred embodiment of the present invention is illustrated in FIGS. 3A and 3B and is generally similar in design to the second hand splint 20 of FIGS. 2A and 2B. Due to the similarity, and in the interests of brevity, only differences in the designs of the second and third illustrated embodiments of the dynamic hand splints 20,30 will be described.

In this regard, the principle difference in design relates to the finger and thumb tensioners and attachment of the finger and thumb tensioners to the sleeves 128,188. Specifically, whereas the tensioners in the second embodiment of the hand splint 20 comprise resilient struts 116,118,120,122,124 such as, for example, strips of spring steel or composite rods, that are secured to the sleeves 128,188 by pockets 130,190, the tensioners of the hand splint 30 of the third embodiment may be thinner and may comprise resilient bands 301 that are secured to the sleeves 128,188 via anchor guides 303,305, 307. In particular, each band 301 is secured to a respective sleeve 128,188 via a plurality of anchor guides 303,305,307 between which the band 301 extends, with an anchor guide 303,305,307 being disposed proximate each phalanx of the respective digit.

Thus, referring to FIG. 3B, a band 301 is illustrated as extending from the attachment mechanism 186 along the finger sleeve 128 covering the index finger. The band 301 is secured to the sleeve 128 by three anchor guides 303,305,307 with each anchor guide 303,305,307 being disposed proximate a separate phalanx of the index finger. Each anchor guide 303,305,307 preferably is formed from a rubber material and defines a slot through which the band 301 is threaded. The last anchor guide 307 further preferably receives and retains an end cap 309 of the band 301 for retention of the end of the band 301 within the anchor guide 307 during closing and opening of the hand.

The bands 301 of the splint 30 of the third embodiment are generally more flexible than the struts 116,118,120,122,124 of the first and second embodiments. Nevertheless, bands having differing elasticity and resilience may be provided and the bands 301 may be changed as desired for providing more or less resistance to the closing of the hand. Additionally, elastic or inelastic bands may be used in accordance with the third embodiment (the elasticity in this regard being in the direction of length of the bands), which additionally contributes to resistance to closing of the hand.

In view of the foregoing, it will be appreciated that several preferred embodiments of dynamic hand splints 10,20,30 of the present invention have been disclosed and described in detail with reference to the drawings. Furthermore, other embodiments having alternative or equivalent features also have been and are disclosed, and equally are within the scope of the present invention. For instance, areas having loops and areas having hooks may be reversed in the aforementioned embodiments. Furthermore, while tensioners have been disclosed as extending along the dorsum of a respective digit, the tensioners may extend instead along a side of the respective digit and may be retained, for example, either in an elongate side pocket or by anchor guides mounted along the side. Moreover, while a single band is disclosed as extending the length of each digit and passing through multiple anchor guides, with segments of the same band extending between each pair of anchor guides, a plurality of smaller bands may extend between the anchor guides in substitution for the segments of the single band, thereby providing a substantially equivalent resistance to bending of the digit.

The invention claimed is:

1. A dynamic hand splint, comprising:
    (a) a forearm support section configured to be releasably attached to a forearm;
    (b) a hand support section connected to the forearm support section;
    (c) a sleeve configured to receive a digit therein; and
    (d) a tensioner having a resilient body extending between a proximal first end and an opposite distal second end, wherein
        (i) the tensioner proximal first end is attached to and extends from the hand support section, and
        (ii) the tensioner resilient body is retained to the sleeve at a first location of the sleeve and at a second location of the sleeve, the first and second locations being spaced apart such that the resilient body spans a joint of the digit when received within the sleeve with the first and second locations being located along a longitudinal axis of the digit on opposite sides of the joint;
    (e) wherein the resilient body has sufficient flexural strength to resist, but not prevent, bending of the digit received within the sleeve such that, when the digit is flexed from an extended position toward a flexed position, the resilient body of the tensioner bends with the digit and the digit is urged by the tensioner toward the extended position, and the tensioner is slidable relative to the sleeve.

2. The dynamic hand splint of claim 1, wherein the tensioner is a fixed length that is not extendable when the digit is flexed from the extended position toward the flexed position.

3. The dynamic hand splint of claim 1, wherein the forearm support section comprises a malleable material and includes a bend therein, whereby the forearm support section is configured to determine an angle at which a wrist will be disposed relative to the forearm when the forearm support section is donned.

4. The dynamic hand splint of claim 1, wherein the tensioner is pivotally mounted to the hand support section for abductional and adductional movement relative to the hand support section.

5. The dynamic hand splint of claim 1, wherein the resilient body of the tensioner is configured to extend along and in parallel with a majority of an overall length of the digit.

6. The dynamic hand splint of claim 1, wherein the sleeve further comprises a first guide that is attached to the sleeve at the first location and a second guide that is attached to the sleeve at the second location, and wherein the tensioner is retained to the sleeve by the first and second guides.

7. The dynamic hand splint of claim 6, wherein each of the first and second guides defines an opening through which the tensioner extends.

8. The dynamic hand splint of claim 7, wherein the tensioner comprises a thin band and the openings of the first and second guides comprise slits through which the band extends.

9. The dynamic hand splint of claim 8, wherein the tensioner is configured to slide relative to the first and second guides.

10. The dynamic hand splint of claim 1, wherein the digit is a finger.

11. A method for donning elements of a dynamic hand splint, comprising:
    (a) attaching a forearm support section and a hand support section to a forearm and donning a sleeve onto a digit of the hand;
    (b) attaching a tensioner having a proximal first end, a distal second end and a resilient body extending therebetween to the hand support section at the proximal first end of the tensioner;
    (c) attaching the tensioner to the sleeve such that the resilient body of the tensioner extends along and spans a joint of the digit and is attached to the sleeve along a longitudinal axis of the digit on opposite sides of the joint; and
    (d) wherein, (i) the resilient body of the tensioner has sufficient flexural strength to resist, but not prevent, bending of the digit, and
(ii) when the digit is flexed from an extended position toward a flexed position, the digit is urged by the tensioner toward the extended position and the tensioner remains positioned over the digit throughout flexion and extension.

12. The method of claim 11, wherein the tensioner comprises a resilient band and the step of attaching the tensioner to the sleeve comprises threading the resilient band through a plurality of guides, each guide being secured to the sleeve for keeping the resilient band off of and out of abutment with one or more joints of the digit during flexion.

13. A dynamic hand splint, comprising:
(a) a forearm support section and a hand support section that are configured to be releasably attached to a forearm;
(b) a plurality of tensioners, each tensioner including a proximal first end, a distal second end and a resilient body extending therebetween, each tensioner being attached to the hand support section at its proximal first end and attached to a respective digit through a respective sleeve in which the respective digit is received such that, when a digit is flexed from an extended position toward a flexed position, each tensioner moves with respect to its respective sleeve and the digit is urged by a respective tensioner toward the extended position; and
(c) wherein each of the plurality of tensioners is slidably attached to the respective sleeve at at least a first location, each tensioner thereby being linearly movable relative to the respective sleeve to allow the tensioner to remain positioned over its respective digit throughout flexion and extension.

14. The dynamic hand splint of claim 13, wherein each tensioner is further slidably retained to the respective sleeve at at least a second location of the respective sleeve, the first and second locations being spaced apart such that the resilient body of each tensioner spans a joint of the respective digit when received within the sleeve, with the first and second locations being located along a longitudinal axis of the respective digit on opposite sides of the joint.

15. The dynamic hand splint of claim 14, wherein each sleeve further comprises a first guide that is attached to the sleeve at the first location and a second guide that is attached to the sleeve at the second location, and wherein each tensioner is retained to the respective sleeve by the first and second guides.

16. The dynamic hand splint of claim 15, wherein each of the first and second guides defines an opening through which the respective tensioner extends.

17. The dynamic hand splint of claim 16, wherein each tensioner comprises a thin band and the openings of the first and second guides comprise slits through which the band extends.

18. The dynamic hand splint of claim 17, wherein each tensioner is configured to slide relative to the corresponding first and second guides.

19. The dynamic hand splint of claim 13, wherein each sleeve includes a pocket that extends substantially along a length of the respective sleeve and each tensioner is slidably received in the pocket of one of the sleeves such that each tensioner slides within the respective pocket as the respective digit undergoes flexion and extension.

* * * * *